US00PP16046P3

(12) United States Plant Patent
Speichert

(10) Patent No.: US PP16,046 P3
(45) Date of Patent: Oct. 18, 2005

(54) ***ARTEMISIA* PLANT NAMED 'GOLDEN PHOENIX'**

(50) Latin Name: *Artemisia vulgaris*
Varietal Denomination: Golden Phoenix

(76) Inventor: C. Greg Speichert, Crystal Palace Perennials, P.O. Box 154, St. John, IN (US) 46373

( * ) Notice: Subject to any disclaimer, the term of this patent is extended or adjusted under 35 U.S.C. 154(b) by 138 days.

(21) Appl. No.: 10/440,579

(22) Filed: May 19, 2003

(65) Prior Publication Data

US 2004/0237162 P1 Nov. 25, 2004

(51) Int. Cl.[7] ..... A01H 5/00

(52) U.S. Cl. ..... Plt./373

(58) Field of Search ..... Plt./263, 373

*Primary Examiner*—Howard J. Locker
(74) *Attorney, Agent, or Firm*—Penny J. Aguirre

(57) ABSTRACT

A new cultivar of *Artemisia vulgaris* 'Golden Phoenix' characterized by chartreuse colored foliage, a moderate growth rate with limited stoloniferous growth, and foliage that is frost hardy.

1 Drawing Sheet

Botanical classification: *Artemisia vulgaris.*
Varietal denomination: 'Golden Phoenix'.

BACKGROUND OF THE INVENTION

The present invention relates to a new and distinct cultivar of *Artemisia* plant, botanically known as *Artemisia vulgaris* and will be referred to hereafter by its cultivar name, 'Golden Phoenix'. 'Golden Phoenix' represents a new Mugwort, a herbaceous perennial herb grown for ornamental use.

The inventor discovered the new cultivar, 'Golden Phoenix', at his nursery in St. John, Ind. in the fall of 2000. The new *Artemisia,* 'Golden Phoenix' was discovered as a naturally occurring whole plant mutation of *Artemisia vulgaris* 'Cragg-Barber Eye' (un-patented). The new cultivar was selected based on the chartreuse color of its foliage. 'Golden Phoenix' differs from the parent plant in that the leaves of 'Golden Phoenix' exhibit a chartreuse to golden coloration that lacks any green markings, whereas the leaves of 'Cragg-Barber Eye' have chartreuse foliage with green flecks and green venation and foliage that is highly variable in color and color pattern among different leaves. The chartreuse foliage of 'Golden Phoenix' does become more golden in higher light conditions but is consistent throughout the plant. 'Golden Phoenix' has also been shown to be less vigorous than is typical for *Artemisia vulgaris*, a trait that will be beneficial for its use as a garden plant.

Asexual reproduction of the new cultivar was first accomplished by terminal stem cuttings in St. John, Ind. in the fall of 2000 by the inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Golden Phoenix' from other varieties in commerce known to the inventor.

1. Foliage color is chartreuse (yellow-green) and the color is consistent throughout the plant without any green markings.
2. The chartreuse color intensifies and becomes more golden under higher light conditions.
3. Moderate vigor with limited stoloniferous growth; more clump-forming than is typical for *Artemisia vulgaris.*
4. Foliage is hardy to frosts and cool temperatures; maintains good coloration until a hard freeze.

BRIEF DESCRIPTION OF THE PHOTOGRAPHS

The plants in the accompanying photographs depict a one-year-old plant grown from stem cutting of 'Golden Phoenix' in a one-gallon container in St. Charles, Ind. The data was taken two months after breaking dormancy and growth under full sun in spring. The colors in the photographs are as true as reasonable possible with the digital photography and reproduction shown and the color values in the botanical description most accurately describe the actual colors of the new *Artemisia.*

The photograph at the top of the sheet illustrates the overall appearance of the new *Artemisia* whereas the photograph at the bottom of the sheet comprises a close-up view of a typical leaf. The upper surface is shown on the left and the lower surface is shown on the right.

DETAILED BOTANICAL DESCRIPTION

The following is a detailed description of the new cultivar as grown in a trial bed for one year from a stem cutting in St. Charles, Ind. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Golden Phoenix' is a cultivar of *Artemisia vulgaris.*

Commercial classification: Mugwort.

Parentage: Naturally occurring whole plant mutation of *Artemisia vulgaris* 'Cragg-Barber Eye', an un-patented cultivar.

General description:

*Blooming period.*—Flowering has not been observed.

*Plant habit.*—When grown in containers from a cutting, the habit is compact and bushy. Habit in the garden after winter dormancy is more upright and spreading.

*Growth rate.*—Moderate with limited spreading through stoloniferous growth.

*Height and spread.*—About 30 cm in width and 30 cm in height in 4 months.

*Hardiness.*—ISDA Zones 4 to 8.

*Culture.*—Grows best in well-drained, fertile soil in full sun.

*Disease resistance.*—*Artemisia vulgaris* is relatively disease free, there has been no disease problems observed for 'Golden Phoenix' when grown in well-drained soil in full sun. A limited amount of black spot was observed on the lower foliage of plants that were grown in wet soils.

*Root description.*—Fleshy, rhizomatous.

Growth and propagation:

*Propagation.*—Terminal stem cuttings (preferred for propagation), rhizome division.

*Root initiation.*—About 10 days at 25° C. air temperature in summer.

*Time required for root development.*—4 weeks to fully develop in a 2.5 in liner in soilless media when grown at 25° C. in a greenhouse without supplemental lighting in summer. A 2.5 in liner will finish in a one-gallon in 2 months under outdoor conditions in spring and summer.

Stem description:

*Shape.*—Quadrangular, solid.

*Stem color.*—New growth; ranges from 144B to 144D, maturing growth; ranges from 144B to 144D with some overlaying coloration of 59C, mature woody growth; 165A.

*Stem size.*—2 to 4 mm in diameter.

*Stem surface.*—Mature stems are glabrous, stems of new growth are tomentulose.

*Internode length.*—Expands to about 1.5 cm in length on mature growth (basal), varies from 0.5 cm to 1.0 cm on new growth (terminal) in the garden under moderate light. Internodes are shorter in higher light with a maximum of about 1.0 cm on mature growth.

*Branching.*—Stems arise from rhizomes, secondary branching (one of two) may be observed on first year growth from cuttings, whereas branching after dormancy in the garden is not as frequent. Stems reach up to about 30 cm in height.

Foliage description:

*Leaf shape.*—Primarily obovate or ovate in outline.

*Leaf size.*—5 to 9 cm in length, 4 to 6 cm at widest point. Individual segments range from 1.0 to 3 cm in length and 0.5 to 1.5 cm in width. Stipule-like lobes are 0.2 to 0.4 cm in width and 0.5 to 1 cm in width.

*Leaf quantity.*—About 15 to 35 per branch.

*Leaf division.*—Pinnatisect. Leaves are deeply incised into ascending, acute, unequal segments that are again incised. Principle clefts are nearly to the mid-rib. Typically, 7 to 9 primary segments with 2 pairs of stipule-like lobes near at base.

*Leaf base.*—Base is blunt at attachment to stem, base of leaf segments are cuneate.

*Leaf apex.*—Terminal leaf segment is tri-dentate with an acute apex.

*Leaf venation.*—Upper surface; N144C in color, distinguishable but not prominent, lower surface; 145D in color, raised above surface.

*Leaf margins.*—Deeply incised.

*Leaf attachment.*—Sessile.

*Leaf arrangement.*—Alternate.

*Leaf surface.*—Upper; glabrous. Lower; dense white-tomentose.

*Leaf color.*—Mature and new growth under moderate light conditions; upper surface is an intermediate color between N144A and N144B, lower surface is 145 C. Mature and new growth under high light conditions on the upper surface is a base N144B overlaid with 153D that is increasing prominent towards the leaf edges, lower surface is a base of 147D with an overlay of 153D on the edges.

*Leaf fragrance.*—Slightly aromatic, mint-like.

Flower description: Inflorescence development has not been observed during the two years of trails as grown in moderately fertile garden soil in full sun in the Midwest. Flowering has not been tested to date under alternative conditions, but flowering may occur under different growing conditions or when grown in a milder climate.

It is claimed:

1. A new and distinct cultivar of *Artemisia* plant named 'Golden Phoenix' substantially as herein illustrated and described.

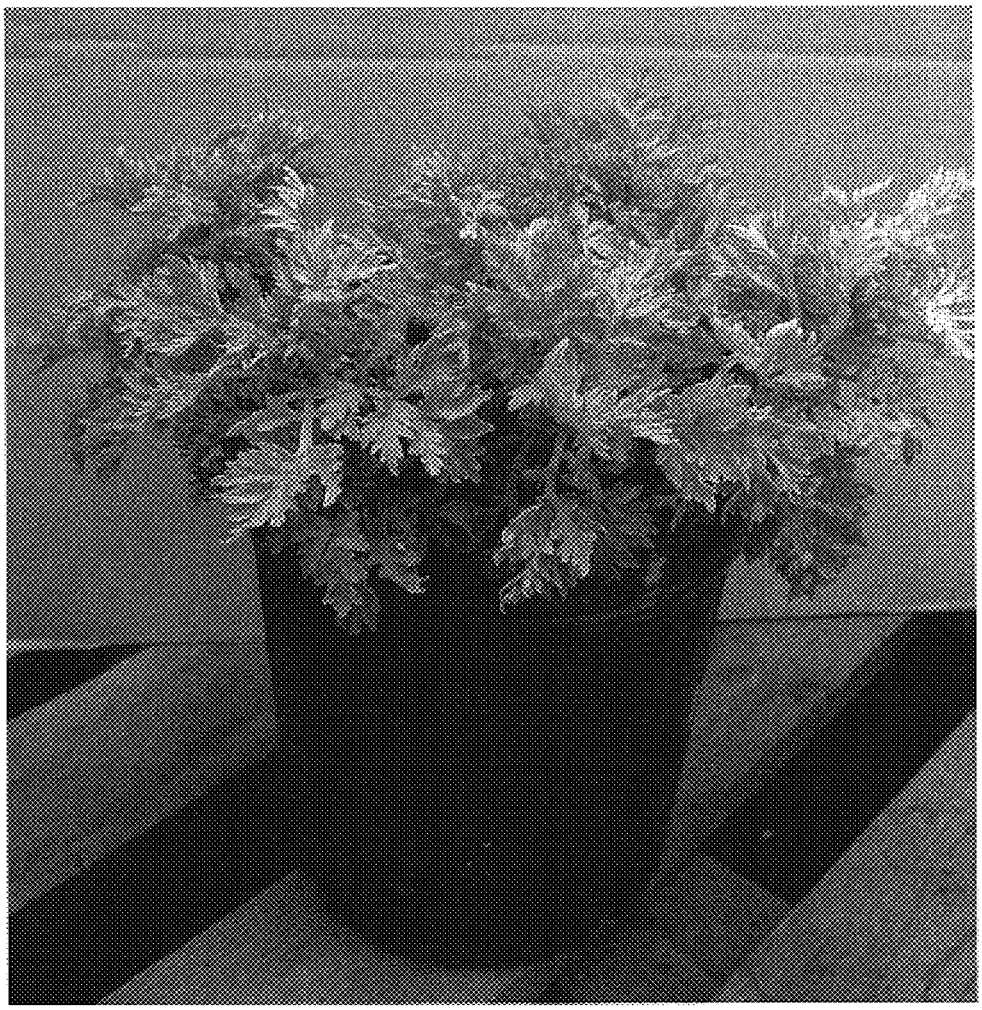
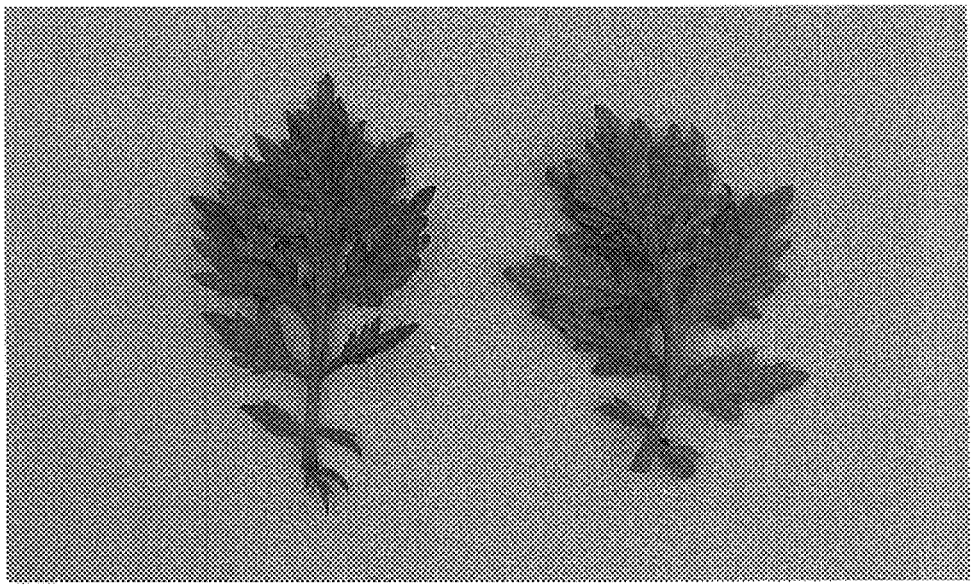

* * * * *